United States Patent [19]
Christie et al.

[11] Patent Number: 5,660,844
[45] Date of Patent: Aug. 26, 1997

[54] COLLAR TO CONTROL ARTHROPOD INFESTATIONS OF ANIMALS

[75] Inventors: Howard Christie, Raytown; Charles S. Pinzino, Kansas City, both of Mo.

[73] Assignee: Pfizer Inc., New York, N.Y.

[21] Appl. No.: 529,276

[22] Filed: Sep. 15, 1995

Related U.S. Application Data

[63] Continuation of PCT/US94/02948, Mar. 18, 1994, continuation of Ser. No. 33,384, Mar. 18, 1993, abandoned.

[51] Int. Cl.$^6$ ............................................. A01N 25/08
[52] U.S. Cl. ........................ 424/411; 424/405; 514/876; 514/919
[58] Field of Search ........................ 424/405, 406, 424/408, 409–412, 438

[56] References Cited

U.S. PATENT DOCUMENTS

| | | | |
|---|---|---|---|
| 2,791,202 | 5/1957 | Doyle | 424/411 |
| 4,792,450 | 12/1988 | Kydonieus | 424/449 |
| 4,879,117 | 11/1989 | Rombi | 424/411 |
| 5,266,324 | 11/1993 | Stendel | 424/411 |
| 5,294,445 | 3/1994 | Sieveking et al. | 424/411 |
| 5,296,227 | 3/1994 | Norval | 424/411 |
| 5,437,869 | 8/1995 | Kelley | 424/406 |

*Primary Examiner*—Neil S. Levy
*Attorney, Agent, or Firm*—Peter C. Richardson; Paul H. Ginsburg; Alan L. Koller

[57] ABSTRACT

The present invention provides a collar containing a novel gel formulation of a wax and linear aliphatic hydrocarbon combination capable of the controlled release of an insecticide such as chlorpyrifos for the control of arthropods infesting animals. FIG. 1 depicts release rate proportional to chlorpyrifos (DURSBAN) concentration.

15 Claims, 6 Drawing Sheets

COLLAR TO CONTROL ARTHROPOD INFESTATIONS OF ANIMALS

This is a continuation of copending application International Application PCT/US94/02948 filed on Mar. 18, 1994 and which designated the U.S. which is a continuation of Ser. No. 08/033,384, filed Mar. 18, 1993, abandoned.

FIELD OF THE INVENTION

This invention relates generally to the field of collars useful in protecting animals against arthropods, and more specifically to novel collars containing an active ingredient.

BACKGROUND OF THE INVENTION

It is customary to treat animals to control and/or avoid insects and pest infestation, particularly fleas and ticks, by spraying the coats of the animals with, or dipping the animals in, an insecticide solution. This type of treatment provides temporary protection, usually lasting about three weeks. After this time period, the treatment may be degraded by light and microorganisms so that its effectiveness decreases.

Other types of insect and pest controls are also known. For example, insecticidal ear tags have recently become a valuable tool for the control of livestock pests. The ear tags release an insecticide, which is spread when the tag rubs against an animal's coat. U.S. Pat. No. 4,606,478 describes such an ear tag, which has a reservoir containing a liquid pesticide. Liquid pesticides are generally undesirable for use in collars, as they can easily be chewed through, releasing the liquid pesticide.

Further, for domesticated pets, such as dogs and cats, collars containing an insecticidal composition have been used to protect these animals against fleas and ticks. However, the protection offered by such collars is unreliable. See, e.g. the device described in U.S. Pat. No. 4,930,451. These collars are also short-lived because the matrix used is a solid, which provides poor efficiency in distribution of the insecticide.

There remains a need in the art for an effective device for protecting animals against ticks and fleas for an extended period of time.

SUMMARY OF THE INVENTION

In one aspect, the present invention provides a device for the controlled, sustained release of a composition useful in protecting an animal against arthropod pests. The novel device comprises a flexible, polymeric reservoir containing an organic gel formulation having dispersed therein an active insecticidal ingredient. The polymeric reservoir is permeable to at least the active ingredient. In one embodiment, the device is in the form of a collar, although other forms are useful, e.g., ear tags.

In still another aspect, the invention provides a method of protecting animals against arthropods, particularly fleas and/or ticks involving the step of providing an animal with a device of the invention. Other aspects and advantages of the present invention are described further in the following detailed description of the preferred embodiments thereof.

DETAILED DESCRIPTION OF THE INVENTION

Figure 1:
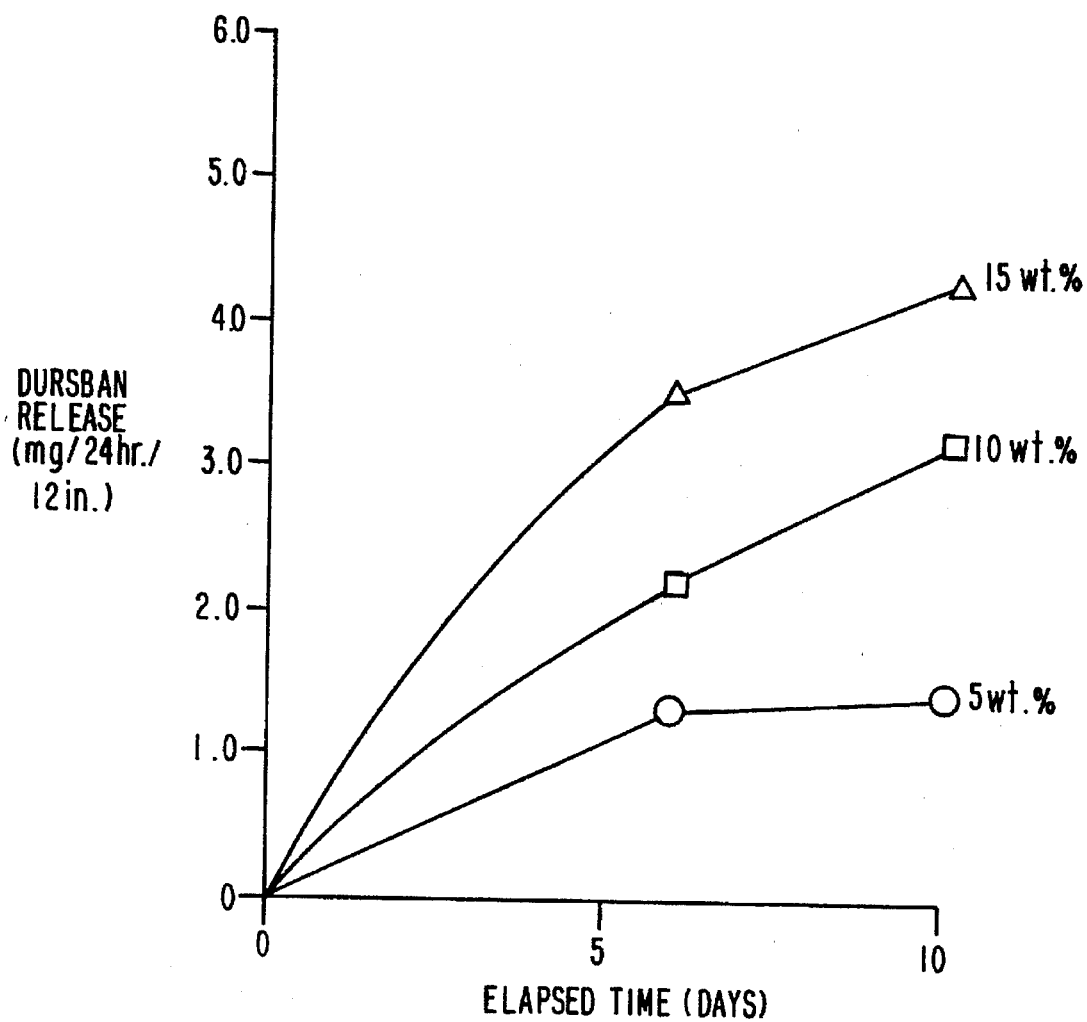
FIG. 1 is a line graph of the pesticide, chlorpyrifos (Dursban®) release versus time for PVC tubing reservoirs containing 5 (○), 10 (□), and 15 (Δ) weight percent Dursban® pesticide in gel described in Example 2.

The present invention provides a novel device capable of providing controlled, continuous release of a composition useful in protecting an animal against arthropods, including mites, flies, ticks, and fleas.

According to this invention the device comprises a reservoir means and a gel matrix contained within the reservoir means. The gel matrix contains a selected insecticidal or pesticidal active ingredient. The device enables sustained release of appropriate amounts of the active ingredient when the reservoir is placed into contact with an animal. The composition in the reservoir continuously permeates through the reservoir and is distributed over the surface of the animal's body by the combination of the nature of the gel and its interaction with the body oil of the animal, and the movement of the device.

The reservoir means of the device of the present invention is preferably formed of a membrane of rigid or flexible polymeric material permeable to at least the active ingredient of a selected insecticidal composition. Although the reservoir membrane may be of a rigid material, a flexible polymeric material is preferred because it can be more easily adapted to fit an animal. Suitable materials include polyamide, flexible polyacrylate, polyvinyl chloride, ethylenevinylacetate, polyolefin, polyurethane, polyamide, and silicone polymers. Particularly desirable are medical-grade silicone rubber tubing or flexible (plasticized) polyvinyl chloride (PVC) tubing, such as that made by Norton Performance Plastics (Tygon® R-3603). Although less desirable because of their rigidity, porous tetrafluoroethylene, polyethylene, and polypropylene polymers may also be used. This lipophilic reservoir material also aids in the distribution of the active ingredient by the body oil of the animal being treating because it is permeable to the body oil (and impermeable to water).

The reservoir membrane must be permeable to the insecticide or other active ingredient used without reacting with it in any significant amount. The reservoir membrane may be of any suitable shape, with an internal cavity sufficient to hold the active ingredient and the reservoir packing material. Preferably the reservoir is tube-shaped. Currently, the preferred delivery device is capable of being wrapped loosely around the neck of an animal, e.g. in a belt-like configuration, a collar. Typically, the reservoir has a length of about 6 to about 24 inches. However, neck bands of other suitable lengths can be easily fabricated. The bands can be provided with any suitable fastening means, e.g. a buckle, velcro, or snaps.

Provided within the reservoir is an insecticidal composition contained within a selected gel, referred to herein as a "gel matrix". As used herein, the term "gel" means a semi-solid, organic gel, i.e., a gel containing an organic solvent, as opposed to a hydrogel, which contains water. The gel of the invention is further characterized by being inert to, or not reacting with, the active ingredient of the insecticidal composition which is contained within the gel matrix. The gel is further described as being well suited for use with lipophilic compounds.

The gel matrix continuously wets the inside surface of the reservoir with the insecticidal composition and is capable of providing a continuous diffusion action, so that at least the active ingredient in the composition is capable of continuously permeating through substantially the entire surface of the polymeric membrane to the outer surface of the reservoir without the presence of any wicking material within or on the reservoir. The gel matrix also provides for the optimum, controlled release of the animal-treating or insecticidal composition from the reservoir.

According to the present invention, the gel matrix composition comprises a combination of a wax and an organic solvent, particularly a linear aliphatic solvent, into which is introduced a selected active ingredient(s). Preferably the wax functions as a gelling agent for the hydrocarbon, i.e., the organic solvent. Preferred waxes are low molecular weight polyethylene waxes which are readily soluble in warm (>140° F.) aliphatic solvents, e.g., polyethylene glycol. Such polyethylene waxes, generally have molecular weights ranging from between 1,800 to 8,000 kD. Waxes of this type are commercially available under the trademark Epolene® [Eastman], having the further designations N-14, C-13, C-15, and C-16, and may be used in this invention. Currently, the preferred wax is Epolene® N-14 wax.

Other suitable waxes may be utilized in the composition of a gel useful in this invention. Also suitable are paraffin waxes, e.g. hydrocarbon waxes, beeswax, animal and vegetable waxes, having a high melting point (>50° C.).

Suitable organic solvents useful in forming the gel of this invention include linear aliphatic ester solvents characterized by at least ten carbons in the chain. The resistance of PVC tubing, which is useful in making the reservoir, to aromatic hydrocarbons is known to be minimal, especially with protracted exposure times. Generally, deleterious effects on PVC tubing, such as plasticizer migration, are reduced as the molecular weight (size) of the aliphatic hydrocarbon solvent increases.

A suitable solvent within the preferred molecular size range therefore can include, n-octane, isooctane, decane, dodecane, hexadecane, and mineral oil (a mixture of $C_{22}$–$C_{26}$ hydrocarbons), and combinations thereof. The size of the solvent molecules is believed to play a significant role in determining the eventual permeation rate of the active ingredient through the reservoir tubing wall. Preferably the higher molecular weight solvents are preferred, e.g., hexadecane and mineral oil. See, Example 2 below. Currently, the preferred solvent, when using polyvinyl chloride (PVC) tubing, is mineral oil or a 80/20 (vol/vol) mixture of hexadecane/mineral oil.

Using the teaching herein, other suitable solvents may be readily selected by one of skill in the depending upon the desired release rate and activity of the selected pesticide. Suitable solvents include those characterized by low toxicity and safety in animals.

Optionally, other additional gelling agents or components may be utilized in the formulation of the gel matrix of this invention. Such optional ingredients include the calcium salts of fatty acids (e.g. calcium distearate) which are relatively low cost and nontoxic.

The gel matrix of the device of this invention contains a selected active ingredient, preferably an active ingredient capable of killing ectoparasites on animals, particularly those common to domesticated cats and dogs. Preferred active ingredients are those soluble in hydrocarbon solvents of the gel. A number of such insecticides are commercially available for this purpose and may be readily obtained and selected by one of skill in the art depending on the identity of the pest or insect, and the animal to be treated. Suitable insecticides include chlorinated hydrocarbons, organophosphates, pyrethroids, and carbamates. Examples of such insecticides are those identified by the common names, lindane, methoxyclor, permethrin, cypermethrin, dichlorvos, diazinion, dioxation, chlorfenvinphos, and bendiocarb. Currently, the preferred active ingredient for treatment of fleas and ticks is a chlorpyrifos. This is available commercially under the trademark Dursban® [Dow Chemical].

The following Table I provides a list of suitable solid insecticides known to those of skill in the art, which may be used in the present invention and their corresponding molecular weights. These insectices are soluble in hydrocarbon solvents and suitable for use on dogs according to the present invention. See, e.g., the Merck Index for the chemical names of these compounds.

TABLE I

| Insecticide | Molecular Weight |
| --- | --- |
| amitraz | 293 |
| phosmet | 317 |
| tetramethrin | 331 |
| chlorpyrifos (g) | 351 |
| bromophos | 386 |
| permethrin (g) | 391 |
| cypermethrin | 416 |
| deltamethrin | 505 |

The gel matrix composition in the reservoir may contain more than one active ingredient, e.g., an insect growth regulator (IGR). Suitable IGRs are well known to those of skill in the art and include such common names and tradenames as methoprene, hydroprene, S-methoprene, S-hydroprene, dimilin (diflupenzeron), SUMILAR™ pyriproxyfen IGR (4-phenoxyphenyl-(RS)-2-(2-pyridyloxy) propyl ether) (Mfr. Sumitomo), NYLAR® pyriproxyfen IGR, and chromazine. See, the Merck Index for the chemical names. The composition within the reservoir containing these active ingredients may include optional conventional additives, e.g. to alter the properties of the insecticide so that it can be maintained in solution or suspension within the gel matrix or to deodorize the composition.

The active ingredient or ingredients are present in the reservoir in excess of the amount required to produce the desired effect to ensure that the appropriate effective amount of the active ingredient is applied to the animal. Generally, an excess of about 1.5 to 3 times the effective amount is required.

In the case of insecticides, such as chlorpyrifos, the amount of active ingredient in the reservoir is generally sufficient to provide about 0.5 mg per day to about 5 mg per day to the animal. The amount of insecticide employed depends upon the size of the animal and the particular insecticide utilized. For example, for a small animal, e.g. about 7 kg, about 0.5 to about 4 mg is preferred. In contrast, for a larger animal, e.g. about 16 kg, about 2 mg to about 6 mg is preferred. With such amounts of insecticide in the reservoir, the device of the invention is capable of delivering an active ingredient onto the surface of an animal over an extended period of time, generally for up to 300 days. Desirably, the time period over which this dose is administered may be adjusted for such environmental factors as the length of insect season in the locale by adjusting the length of the fill (the volume of gel in the tube).

As described in more detail in the examples below, a gel matrix composition of this invention is prepared by heating the selected organic solvent to high temperature, e.g., greater than 140° F., and dissolving the gelling agent in it. The mixture is then cooled to a temperature above its melting point, and the active ingredient is added, mixing slowly. The mixture is then poured into the reservoir and allowed to cool to room temperature. The appropriate temperatures are dependent upon the melting temperature of the solvent and gelling agent, as well as how high a temperature the active ingredient is capable of withstanding without losing its activity.

For example, where the solvent is mineral oil, and the gelling agent is Epolene® wax, the mixture is made at a temperature of between about 125° to about 130° C. Prior to addition of the active ingredient, chlorpyrifos, the mixture is cooled to between about 95° to about 100° C. At about 90° C., the mixture begins to gel. One of skill in the art can readily determine the appropriate temperatures for other desired active ingredients, waxes and solvents without recourse to undue experimentation.

The ratios of wax and organic solvent forming the gel matrix are as follows. The wax is desirably between about 15 to about 20 wt %. Preferably, the wax is Epolene® N-14 wax and is about 17 wt % of the gel matrix in mineral oil or a mixture of hexadecane/mineral oil. Preferably, the solvent is present in between about 60 to about 80 wt % of the gel matrix. Based on the overall studies, the recommended gel for containing the Dursban® chlorpyrifos pesticide, for example, in tube reservoirs consists of 17 wt % Epolene® N-14 wax in mineral oil, or in an 80/20 (vol/vol) mixture of hexadecane/mineral oil (see Example 4 below). The remainder of the gel formulation is the active ingredient or ingredients, which are preferably present in 10–35 wt %. The active ingredient is generally between about 2% and about 35% of the gel matrix, depending upon the potency of the active ingredient upon the target pest.

One advantage offered by the gel matrix of the invention over prior art pest control devices containing liquid pesticides is that the gel of the invention is in semi-solid form, so that when the middle of the reservoir or tube is punctured, e.g., by an animal bite, the pesticide does not pour out of the collar or reservoir. A significant advantage of the present invention is that the lipophilic gel combines well with the animal's body oil, and actually aids in the transfer of the active ingredient from the gel matrix to the animal's body and in distribution of the active ingredient over the animal's body. This advantage is not provided by prior art hydrogels.

Yet another advantage, discussed below in more detail, is that the semi-solid gel of the invention allows a more controlled, sustained release than that obtained with prior art devices which comprise solid or liquid formulations. These prior art solid gels also require a packing material to provide a wicking action to transfer the insecticide or other active ingredients from the collar or other reservoir to the animal's body. There is no such requirement for a semi-solid gel such as that of the present invention.

The device of the present invention, as described above, may be modified by one of skill in the art to accomplish a variety of effects. Of course, the components of the reservoir, and gel matrix, including the active ingredients may be selected depending upon the pest and animal to be treated. Additionally, the release rate of the active ingredient dispersed in a gel matrix from an reservoir according to this invention may be effected as desired by one of skill in the art employing this disclosure. The release rate is related to the tube dimensions, the concentration of the active ingredient or ingredients, and the hydrocarbon mixture in the gel matrix. It is possible to regulate the rate of release of an active ingredient by modifying the amount of solvent in the gel formulation and the pore size of the tube wall.

For example, generally, as the molecular weight of the liquid insecticide increases, the release rate of the tube collar decreases, assuming the thickness of the tubing is constant. Thus, if the active ingredient is a larger molecular weight molecule than chlorpyrifos and the same release rate is desired as for chlorpyrifos, a larger percentage of solvent can be used, or a more porous tube wall can be used. Alternatively, if a lower molecular weight molecule is used, a smaller percentage of solvent can be used, or a less porous tube wall can be used. By adjustment of these parameters, as shown in the paragraph and examples below, the release rate of the active ingredient can be optimized to a desired level.

Using chlorpyrifos for purposes of demonstration, the release rate of the gel, assuming constant tube wall thickness, can be varied by varying the softness (higher solvent content) or hardness (less solvent) of the gel. For example, a soft gel may comprise approximately 15% w/w chlorpyrifos, 12.75% w/w Epolene® N-14 wax, and 72.25% w/w mineral oil. A very hard gel may be made by increasing the gelling agent. An example of a very hard gel is 15% w/w chlorpyrifos, 18.7% w/w Epolene® N-14 wax, and 66.3% w/w mineral oil. A hard gel may be made by using a different liquid carrier. An example of such a hard gel is 15% w/w chlorpyrifos, 12.75% w/w Epolene® N-14 wax, and 72.25% w/w dodecane.

Generally, the preferred tube wall thickness is between 1/32 to 1/8 of an inch, the fill or length of gel in the collar is between 5 to 15 inches in length, with 1 to 5 inch tabs (width) depending upon the size of the dog.

Preferably, when the active ingredient is chlorpyrifos (and the target is ticks and fleas), and it is to be administered to a small animal, as described above, the device of the invention is made to the following parameters. The tube wall thickness (PVC) is between 1/32 to about 1/16 of an inch, the preferred fill length is about 5 to about 10 inches, and the chlorpyrifos is between about 20 to about 25% of the gel matrix. The preferred dose is about 2 mg per day.

The present invention further provides a method of protecting an animal against external parasites, particularly arthropods, and more particularly fleas and ticks, for an extended period of time. This method involves providing an animal with a device of the type described below containing an appropriate insecticide. The device is fastened loosely around the animal's neck by means of a suitable fastening means. The rubbing action of the device against the animal results in the active ingredient being deposited on the animal's coat. Moreover, the interaction between the gel matrix and the body oil of the animal additional aids in the dispersal of the active ingredient from the device and its spread on the animal's coat.

The following examples illustrate the preparation of preferred devices of the invention, including preferred materials for the reservoir, the desired solubility of the preferred active ingredient, Dursban® pesticide, the relationships between tubing/solvent compatibility in the device, solvent permeation rate of the device and gel formation studies and Dursban® pesticide permeation rate studies.

The materials used in the following examples, unless otherwise specified, were: paraffin wax [Paraseal; W&F Mfg]; Epolene® waxes, N-14, C-13, C-15, and C-16 [Eastman]; mineral oil (heavy) [Fisher]; 0-120 Dursban® pesticide (Lot MM 860430 B-P) [Dow Chemical]; n-octane [Phillips Petroleum]; isooctane [Baxter (Burdick and Jackson) No. 232]; decane [J. T. Baker G143]; dodecane [Aldrich 27, 787–9]; hexadecane [Aldrich H 670-3]; xylenes [Fisher X-5[5]]; acetonitrile (UV) [Baxter (Burdick and Jackson) No. 015]; 9-Bromophenanthrene, 96% [Aldrich B7,540-9]; and Tygon® tubing [Norton, R3603]. Due to cost reasons, high-quality, laboratory-grade, flexible PVC tubing was used in these studies. These examples are illustrative only and do not limit the scope of the invention.

EXAMPLE 1

Dursban® (Chlorpyrifos) Solubility Study

Attempts were made to dissolve Dursban® pesticide at 15 wt % in the following solvents at room temperature (27° C.): n-octane, isooctane, decane, dodecane, and mineral oil. A mixture of Dursban® pesticide at 15 wt % in mineral oil was also warmed by running hot tap water on the outside of the vial to note the effect on rate of solution.

Dursban® pesticide at 15 wt % was found to be readily soluble in all solvents tested at 27° C. except mineral oil. Dissolution in mineral oil was accomplished by running hot tap water on the outside of the test vial.

EXAMPLE 2

Tubing/Solvent Compatibility Study

In order to evaluate the compatibility of solvents with the reservoir tubing, ¼-inch lengths of ¼-inch I.D. (⅛-in and 1/16-in wall) R-3603 Tygon® tubing were weighed and placed in small screw-top vials. Initial weights were 0.3 to 0.4 g for the 1/16-in wall samples, and approximated 0.8 to 1.0 g for the ⅛-in wall samples. Each vial contained one ⅛-in wall sample and one 1/16-in wall sample. Triplicate samples were used for each test condition.

Enough solvent (n-octane, isooctane, decane, dodecane, hexadecane, or mineral oil) was added to totally cover the tubing, and the vials were tightly closed. At intervals of 24, 48, and 72 hours (24, 96, 120, and 192 hours for hexadecane), the tubing pieces were removed from the solvent, blotted dry inside and outside with a paper towel, and weighed. Tubing samples were then returned to the solvent. The solvent volume was doubled after the 24-hour weighing. Tubing samples in hexadecane were placed in fresh solvent after the 120-hour weighing.

The mean cumulative percent weight loss for three replicates was determined. Results of the tubing/solvent compatibility studies are reported in Table II. Note that in Table II, the heading Tubing W.T. (in) refers to test specimens of R-3603 Tygon®, ¼-in lengths of ¼-in I.D. tubing of indicated wall thickness (W.T.). The elapsed time column refers to time at the test temperature ambient (about 25° to 27° C.). The % weight loss reported in Table II below used triplicate samples.

As can be seen by reference to Table II below, all tubing samples exhibited some weight loss upon exposure to solvents, probably due to leaching of the plasticizer from the flexible PVC tubing matrix. Samples were observed to become more-opaque and rigid as exposure times increased. These effects were much less pronounced for samples in mineral oil. The percent weight losses of thick-walled samples were significantly less than the percent losses for thin-walled samples. The results shown in Table II indicate that the higher molecular weight solvents—hexadecane and mineral oil—leached plasticizer at a much slower rate than the lower molecular weight solvents.

Polyvinyl chloride tubing (R-3603 Tygon®) is more compatible with higher molecular weight hydrocarbons (mineral oil) and less compatible (ca 10 times) with lower molecular weight hydrocarbons (isooctane), as indicated by weight loss measurements during exposure.

TABLE II

CHEMICAL COMPATIBILITY VIA WEIGHT LOSS OF TYGON® TUBING EXPOSED TO SELECTED HYDROCARBONS

| Solvent (g) | Tubing W.T. (in) | Elapsed time (hr) | Mean cumulative wt loss % |
|---|---|---|---|
| n-Octane | 1/16 | 24 | 14.2 ± 0.0 |
| | | 48 | 17.4 ± 0.1 |
| | | 72 | 19.5 ± 0.2 |
| | 1/8 | 24 | 5.6 ± 0.5 |
| | | 48 | 10.6 ± 0.5 |
| | | 72 | 13.7 ± 0.4 |
| Isooctane | 1/16 | 24 | 21.4 ± 0.7 |
| | | 48 | 28.1 ± 0.2 |
| | | 72 | 29.9 ± 0.0 |
| | 1/8 | 24 | 9.2 ± 0.2 |
| | | 48 | 18.3 ± 0.2 |
| | | 72 | 24.4 ± 0.2 |
| n-Decane | 1/16 | 24 | 19.6 ± 1.1 |
| | | 48 | 27.3 ± 0.1 |
| | | 72 | 28.5 ± 0.1 |
| | 1/8 | 24 | 7.0 ± 0.8 |
| | | 48 | 15.8 ± 0.8 |
| | | 72 | 22.5 ± 0.8 |
| Dodecane | 1/16 | 24 | 13.9 ± 1.1 |
| | | 48 | 23.5 ± 0.8 |
| | | 72 | 27.4 ± 0.3 |
| | 1/8 | 24 | 6.2 ± 0.4 |
| | | 48 | 10.5 ± 0.7 |
| | | 72 | 15.3 ± 0.8 |
| Hexadecane | 1/6 | 24 | 7.3 ± 0.2 |
| | | 96 | 17.1 ± 0.6 |
| | | 120 | 19.5 ± 0.3 |
| | | 192 | 24.0 ± 0.5 |
| | 1/8 | 24 | 4.0 ± 0.3 |
| | | 96 | 7.3 ± 0.9 |
| | | 120 | 8.2 ± 1.0 |
| | | 192 | 10.8 ± 1.3 |
| Mineral oil | 1/16 | 24 | 2.2 ± 0.0 |
| | | 48 | 3.1 ± 0.1 |
| | | 72 | 3.9 ± 0.0 |
| | 1/8 | 24 | 1.3 ± 0.0 |
| | | 48 | 1.8 ± 0.1 |
| | | 72 | 2.2 ± 0.1 |

EXAMPLE 3

Solvent Permeation Rate Studies

Tygon® tubing (¼-in or ⅜-in I.D.) was cut into 14-cm lengths. A 1½-in piece of stainless steel rod of appropriate diameter was inserted 2 cm into one end of the tubing. Two braids of copper wire were tightened around the tubing to secure the stainless steel plug and prevent leaks. Weights of the tube reservoirs were determined with hardware needed to plug the open end. Solvent was charged into the reservoir and the remaining open end sealed as described above. The reservoir length was 10.0 cm. Tube reservoirs were reweighed and suspended vertically in a hood at 24° to 27° and monitored at intervals for weight loss (due to permeation and evaporation of the solvent). Mineral oil-containing reservoirs were wiped with a paper towel prior to each weighing.

A summary matrix for these studies is given in Table III. The isooctane study was replicated as a check. All tubing reservoir weights are ±10 mg.

| Solvent | I.D. (in) | Tubing[a] W.T.[b] (in) | Duration (hr) |
|---|---|---|---|
| n-Octane | 1/4 | 1/16; 1/8 | 187 |
| Isooctane | 1/4 | 1/16; 1/8 | 187 |
| n-Decane | 1/4 | 1/16; 1/8 | 187 |
| Dodecane | 1/4 | 1/16; 1/8 | 187 |
|  | 1/4 | 1/32 | 284 |
|  | 3/8 | 1/16 | 284 |
| Hexadecane | 1/4 | 1/16; 1/8 | 264 |
|  | 1/4 | 1/32 | 285 |
|  | 3/8 | 1/16 | 285 |
| Xylenes | 1/4 | 1/16 | 15 |
| Mineral Oil | 1/4 | 1/32 | 164 |
|  | 3/8 | 1/16 | 260 |

[a]Permeation tests through R-3603 Tygon® Tubing; 10 cm reservoir length; 14 cm overall tubing length.
[b]W.T. = Wall thickness.

The cumulative weight losses (g) versus time (days) for R-3603 Tygon® tubing reservoirs filled with various hydrocarbon solvents at selected intervals are summarized in Table IV.

TABLE IV

CUMULATIVE WEIGHT LOSS (g) OF TYGON® TUBING RESERVOIRS CONTAINING VARIOUS HYDROCARBONS

| Solvent | Tubing reservoir[a] I.D. × W.T. (in) | Elapsed time (days ± 4 hr)[b] | | | | | |
|---|---|---|---|---|---|---|---|
|  |  | 1 | 2 | 4 | 8 | 11 | 28 |
| n-Octane | 1/4 × 1/16 | 0.47 | 0.85 | 1.37 | 1.82 | ND[c] | ND |
|  | 1/4 × 1/8 | 0.02 | 0.22 | 0.61 | 1.40 | ND | ND |
| Isooctane | 1/4 × 1/16 | 0.08 | 0.29 | 0.66 | 1.12 | ND | ND |
|  | 1/4 × 1/8 | <0.01 | <0.01 | 0.09 | 0.53 | ND | ND |
| Decane | 1/4 × 1/16 | 0.16 | 0.41 | 0.76 | 1.19 | ND | ND |
|  | 1/4 × 1/8 | <0.01 | 0.03 | 0.27 | 0.77 | ND | ND |
| Dodecane | 1/4 × 1/32 | 0.21 | 0.37 | 0.49 | 0.64 | 0.72 | ND |
|  | 1/4 × 1/16 | 0.03 | 0.11 | 0.41 | 0.69 | ND | ND |
|  | 1/4 × 1/8 | <0.01 | <0.01 | 0.05 | 0.30 | ND | ND |
|  | 3/8 × 1/16 | 0.01 | 0.30 | 0.59 | 0.94 | 1.11 | ND |
| Hexadecane | 1/4 × 1/32 | <0.01 | 0.04 | 0.03 | 0.17 | 0.22 | ND |
|  | 1/4 × 1/16 | <0.01 | ND | 0.02 | 0.11 | 0.13 | 0.44 |
|  | 1/4 × 1/8 | <0.01 | ND | <0.01 | 0.01 | 0.02 | 0.20 |
|  | 3/8 × 1/16 | <0.01 | <0.01 | 0.03 | 0.13 | 0.19 | ND |
| Xylene | 1/4 × 1/16 | 1.58[d] | ND | ND | ND | ND | ND |
| Mineral oil | 1/4 × 1/32 | <0.01 | <0.01 | <0.01 | <0.01 | ND | ND |
|  | 3/8 × 1/16 | <0.01 | <0.01 | <0.01 | <0.01 | ND |  |

[a]10-cm lengths of R-3603 Tygon® tubing
[b]Exposure temperature 24° to 27° C.
[c]ND = not determined
[d]Elapsed time-15 hr.

Permeation rates were slowed for all solvents as the reservoir wall thickness increased. Permeation rates increased for a given solvent when the reservoir surface area was greater due to a larger inside diameter. Branched hydrocarbons were slower to permeate than linear hydrocarbons for a given wall thickness. Permeation rates decreased as the hydrocarbon chain length increased: mineral oil (C22 to C24)<hexadecane (C16)<dodecane (C12) <decane (C10)<octane (C8). Xylene, an aromatic hydrocarbon, had a permeation rate nearly 5 times that of octane.

Exact breakthrough times for each solvent (the time at which the solvent saturates or comes through the outside of the tube) could not be determined due to variability in the weighing interval schedule.

The permeability of R-3603 Tygon® to hydrocarbons is related to the degree of branching, the chain length, and the aromaticity of the hydrocarbons.

EXAMPLE 4

Gel Formation Studies

Various combinations of four different polyethylene waxes with three high molecular weight hydrocarbon solvents (>$C_{10}$) were tested for their ability to form suitable gels. Solutions were made by heating 50-g mixtures containing 5 to 25 wt % wax in solvent until the wax was totally dissolved. Mixtures were allowed to cool and were observed for cloud point temperature and gel formation. Heating was accomplished with a hot plate, steam bath, or oil bath, depending on the solvent. The waxes tested were paraffin wax and Epolene® waxes N-14 (M.W.=1,800), C-15 (M.W.=4,000), and C-16 (M.W.=8,000). The solvents tested were dodecane, hexadecane, and mineral oil. One gram of a silicone dioxide, such under the trademark CAB-O-SIL® N70-TS [Cabot Corp.] alone and with 4 drops of either polyethylene glycol monooleate or Zonyl® FSK fluorosurfactant [DuPont] was added as a possible thickener for the 20 wt % paraffin in dodecane mixtures. A summary test matrix for these studies appears in Table V.

TABLE V

GEL FORMATION TEST MATRIX

| Wax | Wt % | Solvent |
|---|---|---|
| Paraffin | 5, 10, 20 | Mineral oil |
| Paraffin | 20 | Dodecane |
| Epolene C-15 | 5 | Mineral oil |
| Epolene C-15/N-14 | 5/5 | Mineral oil |

TABLE V-continued

GEL FORMATION TEST MATRIX

| Wax | Wt % | Solvent |
| --- | --- | --- |
| Epolene C-15/N-14 | 5/10 | Mineral oil |
| Epolene C-15/N-14 | 1/15 and 2/15 | Mineral oil |
| Epolene C-16 | 5 | Mineral oil |
| Epolene C-16/N-14 | 2.5/2.5 and 5/5 | Mineral oil |
| Epolene N-14 | 5, 15, 20, 25 | Mineral oil |
| Epolene N-14 | 10, 15, 20 | Dodecane |
| Epolene N-14 | 10 | Hexadecane |
| Epolene N-14 | 10 | Hexadecane/dodecane 50/50 vol/vol |
| Epolene N-14 | 15 | Hexadecane/mineral oil 80/20 vol/vol |

Results of the gel formation studies are summarized in Table VI. Addition of 1 g CAB-O-SIL® N70-TS to a reheated mixture of 20 wt % paraffin in dodecane did not aid gel formation. Polyethylene glycol monooleate and Zonyl® FSC fluorosurfactant were not miscible with the mixture. Preliminary observations indicated that after reheating a mixture of dodecane and 15 wt % N-14 Epolene® wax to solution point, the gel did not reappear upon cooling. Also, when the gel formed by 15 wt % N-14 wax in 80/20 hexadecane/mineral oil was reheated to solution point, the gel reformed upon cooling, but was easily broken by stirring with a glass rod. Extreme thermal cycling should be avoided.

The results indicated that a presently preferred gel for containing Dursban® pesticide in tube reservoirs consists of 17 wt % Epolene® N-14 wax in mineral oil, or in an 80/20 (vol/vol) mixture of hexadecane/mineral oil.

Consistency is measured with a Koehler penetrometer K19500. The penetration readings range from 5 to 40 mm for the various composition and processing conditions used.

TABLE VI

GEL FORMATION STUDIES

| Wax | Wt % | Solvent | Cloud point[a] (°F.) | Remarks |
| --- | --- | --- | --- | --- |
| Paraffin | 5 | Mineral oil | 84.5 | No gel formed |
|  | 10 |  | 91 to 93 | No gel formed |
|  | 20 |  | ~108 | 920° -gel-like, very soft |
|  | 20 | Dodecane | ~91 | Wax ppt out, no |
| Epolene | 5/5 | Mineral oil | ~192 | Wax ppt out, no gel formed |
| Epolene C-15/N-14 | 5/5 |  | ~222 | Slurry-like, no gel formed |
|  | 5/10 |  | ~213 | No gel formed |
|  | 1/15 |  | ~200 | Still pourable |
|  | 2/15 |  | ~216 | Gel-like 1340 |
| Epolene C-16 | 5 | Mineral oil | ~192 | Wax ppt out, no gel formed |
| Epolene C-16/N-14 | 2.5/2.5 |  | ~186 | Viscous liquid, no gel formed |
|  | 5/5 |  | ~220 | No gel formed, wax ppd out |
| Epolene | 5 | Mineral oil | ~192 | No gel formed |
|  | 15 |  | ~212 | Still pourable at 102° |
|  | 20 |  | ~212 | ~116° gel |
|  | 25 |  | ND[b] | Waxy solid-- too stiff |
|  | 10 | Dodecane | ~180 | 85° grease-like gel |
|  | 15 |  | ~181 | Gel-like but too stiff |
|  | 20 |  | ~188 | 155°— hard waxy solid |
|  | 10 | Hexadecane | ~185 | 136°— still fluid |
|  | 10 | Rexadecane/ dodecane 50/50 (vol/vol) | ~185 | 136°— still fluid |
|  | 15 | Hexactecane/mineral oil 80/20 (vol/vol) | ~194 | 155°--not pourable, soft gel-like |

[a] Cloud point in this study is the temperature at which first signs of clouding/opacity were observed at a regular monitoring interval during cooling.
[b] ND = not determined.

EXAMPLE 5

Dursban® Pesticide Permeation Rate Studies

A. The Test Matrix

For the following studies, the matrix is summarized in Table VII. Gel/solvent I is 100% mineral oil. Gel/solvent II is 17 wt % N-14 Epolene® wax in 80/20 (vol/vol) hexadecane/mineral oil. Gel/solvent III is 18 wt % in 80/20 (vol/vol) dodecane/mineral oil. The tubing reservoir was Tygon® R-3603 with a 10 cm reservoir and a 14 cm overall tubing length.

TABLE VII

DURSBAN® PESTICIDE PERMEATION RATE TEST MATRIX

| Gel/ | Tubing Reservoir* | | |
|---|---|---|---|
| solvent | I.D. (in) | W.T. (in) | Dursban® (wt %) |
| I | 1/4 | 1/16 | 0,10 |
| II | 1/4 | 1/16 | 0,10 |
| II | 1/4 | 1/8 | 0,10 |
| III | 1/4 | 1/32 | 0,10 |
| III | 1/4 | 1/16 | 0, 5, 10, 15 |
| III | 1/4 | 1/8 | 0, 5, 10, 15 |
| III | 3/8 | 1/16 | 0,10 |

B. Values in Tables

All values given in the tables below represent the average of duplicate reservoir samples. Dursban® pesticide release values are based on the total Dursban® pesticide removed from the reservoir surface after a specified time interval (usually 18 to 30 hours, except when expanded by weekends or holidays) by rinsing with acetonitrile. These values, derived from gas chromatograph analysis of selected individual rinses are normalized to milligrams per 24 hours. The 24-hour values are then adjusted to project data for reservoir samples 12 inches in length by using a factor derived from the ratio of the corresponding reservoir lengths. Formulas for these adjustments are given below.

a. Length adjustment used to compensate for end diffusion effects:

$L_A = L + 2[2(W.T.)]$, where L=length in cm and W.T.= tubing wall thickness in cm b. Normalized release rate (for 24-hr periods:

$R_{24\ hr} = W(24/T)$, where W=total weight of Dursban® pesticide detected in the rinse in mg; and T=time since previous rinse in hours c. Ratio of adjusted lengths factor:

$F = (L_A$ for 12 in length/$L_A$ for 10 cm length). The units for $L_A$ in both cases must be the same.

d. Adjusted release rate (for 12-in length):

$R_A = (R_{24\ hr})(F)$, where $R_{24\ hr}$=the 24-hour normalized release rate in mg/24 hr; F=2.926 for 1/16-in W.T. tubing or 2.906 for 1/8-in W.T. tubing or 3.038 for 1/32-in W.T. tubing e. Surface area of tube reservoir:

$SA = \pi DL_A$, where D=outside diameter of the tubing in cm; $L_A$=adjusted length in cm. The formula for the effective surface area of a tube reservoir is included here as a point of general information.

Weight loss values are cumulative and represent the weight lost from the reservoir samples due to repeated rinsing. The weight loss is due to three effects: (1) leaching and removal of plasticizer from the tubing during rinses, (2) evaporation or removal of the gel solvent which has diffused through the tubing to the surface, and (3) removal of Dursban® pesticide which has diffused to the surface and is removed by rinsing. All reservoir weight loss values are ±10 mg.

C. Test Specimen Preparation and Sample Collection

The test specimens were prepared and samples collected as follows: Epolene® N-14 wax/solvent mixtures were heated to about 221° F. on an oil bath until all the wax was dissolved. Dursban® pesticide at 10 or 15 wt % was added to the mixtures, and the mixtures were allowed to reheat to 221° F. with stirring. The hot homogeneous mixtures were poured into 10-cm Tygon® tubing reservoirs. Duplicates were prepared for each condition tested (See Example 3 above for preparation and sealing of tubing reservoirs.)

Ten grams of 15 wt % Dursban® pesticide in Epolene® wax/mineral oil gel contain 1.5 g Dursban® pesticide and 8.5 g of gel (1.45 g Epolehe® wax plus 7.05 g mineral oil). The reservoirs were weighed before and after filling and suspended horizontally in a hood. Tube reservoir samples were rinsed daily with ~20 mL of acetonitrile from a wash bottle and weighed.

Reservoir samples from the studies described in Sections E and F below were rinsed daily except for weekends and holidays. Reservoir samples from the study described in Section G were rinsed daily including weekends. Rinses were quantitatively transferred to storage bottles for later analysis. Each rinse was analyzed as a separate sample. Empty tubing reservoirs and tubing reservoirs containing solvent/wax gel were rinsed and weighed along with the Dursban® pesticide-containing samples to serve as controls for weight loss and gas chromatograph (GC) monitoring. The test temperature ranged from 24° to 27° C. during the course of these studies.

D. Gas Chromatograph Analysis of Rinse Samples

A Varian Model 3700 gas chromatograph, equipped with an electron capture detector and a Model 8000 autosampler, was used to analyze the sample rinses. The injector temperature was 250° C. and the detector temperature was 300° C.; the nitrogen carrier gas flow rate was 30 mL/minute. The sample rinses had been brought to a known volume with acetonitrile (50 mL), then diluted (5 mL to 50 mL) to include the internal standard. The final concentration of the internal standard, 9-Bromophen anthrene, was 3 µg/mL. A glass column (2 m×2 mm I.D.) packed with 3% SE-30 on Chromosorb W HP (80 to 100 mesh) was programmed with an oven temperature ramp of 170° C. for 3 minutes, then 170° to 270° C. at 10°/minute. The sample injection volume was 1 µL. The attenuation was 128 at a range of 10.

TABLE XIII

GAS CHROMATOGPAPHIC ANALYSIS SYSTEM

| | |
|---|---|
| GC: | Varian Model 3700 Gas Chromatograph |
| AUTOSAMPLER: | Varian Model 8000 |
| DETECTOR: | Varian Electron Capture (ECD) |
| RECORDER: | Soltec Model 1241 |
| DATA SYSTEM: | Nelson Analytical Model 4400 Chromatography Data System with Model 761S Interface |
| COLUMN: | 3% SE-30 on 80/100 Chromosorb W HP,2 m, 2 mm I.D. |
| CARRIER: | Nitrogen, 30 mL/min |
| INJECTOR: | 250° C. |
| DETECTOR: | 300° C., range 10, attenuation 128 |
| COLUMN: | 170° C. for 3 min, 170° to 270° C. at 10°/min, hold 0 min |
| RUN TIME: | 14 min |
| INJ. VOLUME: | ~1 µL |

The retention times, peak areas, and internal standard quantitations were determined with a Nelson Analytical Model 4400 Chromatography Data System. The retention times for chlorpyrifos and 9-bromophenanthrene (internal standard) were 5.0 and 6.2 minutes, respectively. Standard solutions of chlorpyrifos in acetonitrile were prepared at seven levels by serial dilution and were analyzed concurrently with samples. A check standard was analyzed to assess accuracy of standard preparation and typically agreed within 1.5% of the calibration standard. For the range 0.0205 to 2.05 ppm (equivalent to 0.01025 to 1.025 mg/50 mL rinse sample), point to point calibration was utilized with accuracies of the initial standard injections (back calculation) typically ranging from 97% to 106%.

Detector responses at concentrations greater than 4 ppm were not linear. Therefore, a second order curve was utilized for concentrations from 2.05 to 20.5 ppm (equivalent to 1.025 to 10.25 mg/50 mL rinse sample). Accuracies from this curve were typically 100% to 108%.

E. Dursban® Pesticide Release Rate Studies

1. The first set of Dursban® pesticide release rate studies was designed to show that (1) Dursban® pesticide could migrate through Tygon® R3603 tubing and accumulate on the surface, (2) rinsing the tube reservoir surface with acetonitrile would remove the Dursban® pesticide, and (3) the amount of Dursban® pesticide in the rinse could be quantitated by GC analysis. Each sample was rinsed with acetonitrile 39 times over a period of 55 days.

Table IX summarizes the results of these studies and demonstrates the efficacy of the reservoir release system and the analytical technique. In Table IX, 10 wt % Dursban® pesticide was used; mineral oil with no Epolene® was used in the collar with ¼ in I.D.×1/16 in W.T.×10 cm reservoir length.

TABLE IX

DURSBAN® PESTICIDE RELEASE RATE STUDIES

| Elapsed time (days) | 3 | 6 | 9 | 15 | 19 | 22 | 50 |
|---|---|---|---|---|---|---|---|
| Number of rinses | 3 | 6 | 9 | 12 | 15 | 13 | 34 |
| Dursban® released (mg/24 hr/12 in) | 0.01 | 0.06 | 0.25 | 0.33 | 0.99 | 0.97 | 1.42 |
| Cum. wt. Loss (mg): | | | | | | | |
| Sample[1] | 75 | 125 | 190 | 215 | 235 | 255 | 400 |
| Control[2] | 80 | 120 | 170 | 220 | 230 | 280 | 420 |

[1]Sample = 10% Dursban® pesticide
[2]Control = 0% Dursban® pesticide

2. The next set of Dursban® pesticide release rate studies was designed to show that (1) Dursban® pesticide was compatible with a polyethylene wax gel matrix, (2) the presence of a solvent with a higher permeation rate through Tygon® would accelerate the migration of Dursban® pesticide to the reservoir surface, and (3) increasing the wall thickness of the reservoir would slow the migration of Dursban® pesticide to the surface. The Dursban® pesticide/gel mixture and tube reservoirs were prepared as described above in Section C (18 wt % N-14 Epolene® Wax in 80/20 vol/vol dodecane/mineral oil). Dursban® pesticide was quite soluble in the hot wax/solvent mixture, and the mixture could be safely handled and poured at a temperature well below the decomposition temperature of Dursban® pesticide. Each sample was rinsed with acetonitrile 33 times over a period of 40 days. Results of this set of studies are given in Table X.

A comparison of values in Table X with those in Table IX for similar time intervals clearly shows that the presence of hexadecane ($C_{16}$) significantly increases the release rate of Dursban® pesticide. A comparison of values in Table X for 1/16-in W.T. versus 1/8-in W.T. tubing clearly demonstrates that the thicker wall significantly retards the migration of Dursban® pesticide to the surface. The conditions in Table X include 10 wt % Dursban® pesticide; 17 wt % N-14 wax in 80/20 hexadecane/mineral oil.

TABLE X

DURSBAN® PESTICIDE RELEASE RATE STUDIES[a]

Tubing - 1/4-in I.D. × 1/16-in W.T

| Elapsed time (days) | 3 | 6 | 6 | 13.5 | 19 | 22 | 35 |
|---|---|---|---|---|---|---|---|
| Number of rinses | 2 | 5 | 7 | 11 | 14 | 17 | 28 |
| Dursban® released (mg/24 hr/12 in) | 0.01 | 0.45 | 1.31 | 3.06 | 3.60 | 3.65 | 3.12 |
| Cum. wt. loss (mg): | | | | | | | |
| Sample | 60 | 135 | 220 | 320 | 405 | 495 | 665 |
| Control | 50 | 140 | 230 | 340 | 410 | 490 | 600 |

Tubing - 1/4-in I.D. × 1/8-in W.T.

| Elapsed time (days) | | 7 | 13 | 18 | 21 | 34 |
|---|---|---|---|---|---|---|
| Number of rinses | 7 | 11 | 14 | 17 | 28 | |
| Dursban released (mg/24 hr/12 in) | 0.000.02 | 0.10 | 0.28 | 1.03 | | |
| Cum. wt. Loss (mg): | | | | | | |
| Sample | 200 | 290 | 350 | 425 | 625 | |
| Control | 200 | 280 | 350 | 420 | 600 | |

[a]Reservoir length = 10 cm, total length = 14 cm.

Sample is 10% Dursban® pesticide. Control is 0% Dursban® pesticide.

3. The final set of Dursban® pesticide release rate studies was designed to investigate the effect of Dursban® pesticide concentration on its release rate, and to further explore the effects of tubing wall thickness and solvent on the migration rate of Dursban® pesticide though Tygon® tubing. Each sample was rinsed with acetonitrile daily for 15 days. Results of these studies are summarized in Tables XI through XIV. These experiments used 18 wt % Epolene® N-14 Wax; 80/20 (vol/vol) dodecane/mineral oil.

TABLE XI

DURSBAN® PESTICIDE RELEASE RATE STUDIES[a]

| 5 w % Dursban® pesticide | 1/4-in I.D. × 1/16-in W.T. | | | 1/4-in I.D. × 1/8-in W.T. | | |
|---|---|---|---|---|---|---|
| Elapsed time (days) | 2 | 6 | 10 | 2 | 6 | 10 |
| Number of rinses | 2 | 6 | 10 | 2 | 6 | 10 |
| Dursban® released (mg/24 hr/12 in) | 0.10 | 1.33 | 1.42 | 0.01 | 0.04 | 0.11 |
| Cum. wt. Loss (mg): | | | | | | |
| Sample | 185 | 520 | 925 | 85 | 250 | 405 |
| Control | 210 | 520 | 690 | 80 | 240 | 450 |

[a]Sample is 10% Dursban® pesticide. Control is 0% Dursban® pesticide.

TABLE XII

DURSBAN® PESTICIDE RELEASE RATE STUDIES[a]

| 10 wt % Dursban® pesticide | 1/4-in I.D. × 1/32-in W.T. | | | 1/4-in I.D. × 1/16-in W.T. | | |
|---|---|---|---|---|---|---|
| Elapsed time (days) | 2 | 6 | 10 | 2 | 6 | 10 |
| Number of rinses | 2 | 6 | 10 | 2 | 6 | 10 |
| Dursban® released (mg/24 hr/12 in) | 5.74 | 5.72 | 4.64 | 0.21 | 2.67 | 3.19 |
| Cum. wt. Loss (mg): | | | | | | |
| Sample | 245 | 495 | 630 | 160 | 500 | 715 |
| Control | 210 | 440 | 540 | 210 | 520 | 690 |

[a]Sample is 10% Dursban® pesticide. Control is 0% Dursban® pesticide.

TABLE XIII

DURSBAN® PESTICIDE RELEASE RATE STUDIES[a]

| 10 wt % Dursban® pesticide | 1/4-in I.D. × 1/8-in W.T. | | | 3/8-in I.D. × 1/16-in W.T. | | |
|---|---|---|---|---|---|---|
| Elapsed time (days) | 2 | 6 | 10 | 2 | 6 | 10 |
| Number of rinses | 2 | 6 | 10 | 2 | 6 | 10 |
| Dursban® released (mg/24 hr/12 in) | 0.06 | 0.07 | 0.22 | 0.23 | 4.73 | 4.59 |
| Cum. wt. Loss (mg): | | | | | | |
| Sample | 90 | 240 | 420 | 200 | 645 | 945 |
| Control | 80 | 240 | 450 | 230 | 670 | 920 |

[a]Sample is 10% Dursban® pesticide. Control is 0% Dursban® pesticide.

TABLE XIV

DURSBAN® PESTICIDE RELEASE RATE STUDIES[a]

| 15 wt % Dursban® pesticide | 1/4-in I.D. × 1/16-in W.T. | | | 1/4-in I.D. × 1/8-in W.T. | | |
|---|---|---|---|---|---|---|
| Elapsed time (days) | 2 | 6 | 10 | 2 | 6 | 10 |
| Number of rinses | 2 | 6 | 10 | 2 | 6 | 10 |
| Dursban® released (mg/24 hr/12 in) | 0.13 | 3.52 | 4.25 | 0.02 | 0.06 | 0.19 |
| Cum. wt. Loss (mg): | | | | | | |
| Sample | 135 | 435 | 630 | 90 | 205 | 360 |
| Control | 210 | 520 | 690 | 80 | 240 | 450 |

[a]Reservoir length = 10 cm total length.

Figure 2:
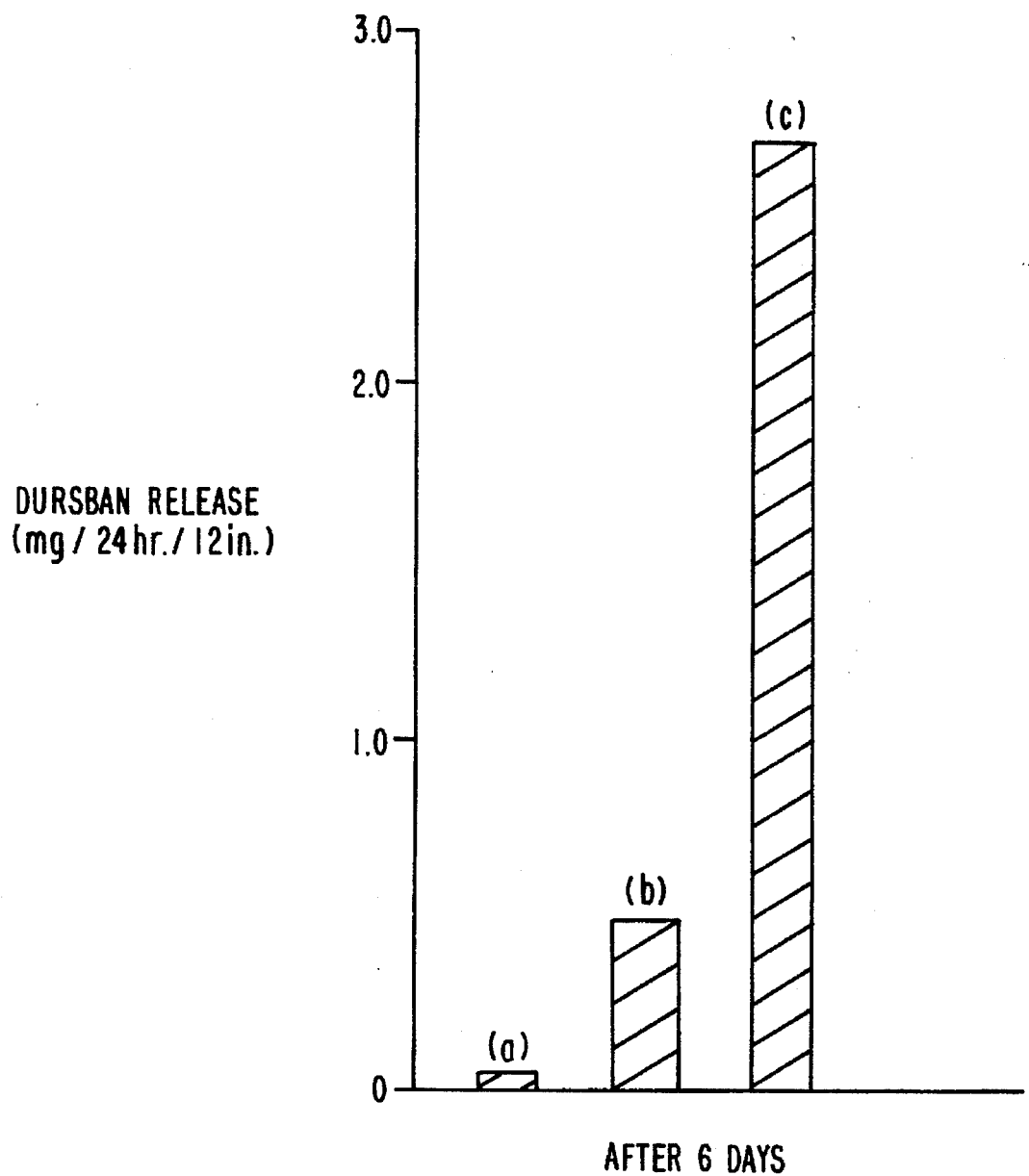
FIG. 2 is a bar graph comparing Dursban® pesticide release from PVC tubing reservoirs containing 10 weight percent Dursban® pesticide in (a) mineral oil, (b) 17 weight percent Epolene® N-14 wax in 80/20 hexadecane/mineral oil, and (c) 18 weight percent Epolene® N-14 wax in 80/20 dodecane/mineral oil described in Example 3.

The release rate of Dursban® pesticide is approximately linear with concentration as illustrated in FIG. 1. FIG. 2 illustrates the effect of the gel (solvent) on the Dursban® pesticide release rate after 6 days (24° to 27° C.) at an initial Dursban® pesticide concentration of 10 wt %, and demonstrates the "carrier" effect that the lower-chain length hydrocarbons have in moving Dursban® pesticide to the reservoir surface: dodecane ($C_{12}$)>hexadecane ($C_{16}$)>mineral oil ($C_{22-26}$).

Figure 3:
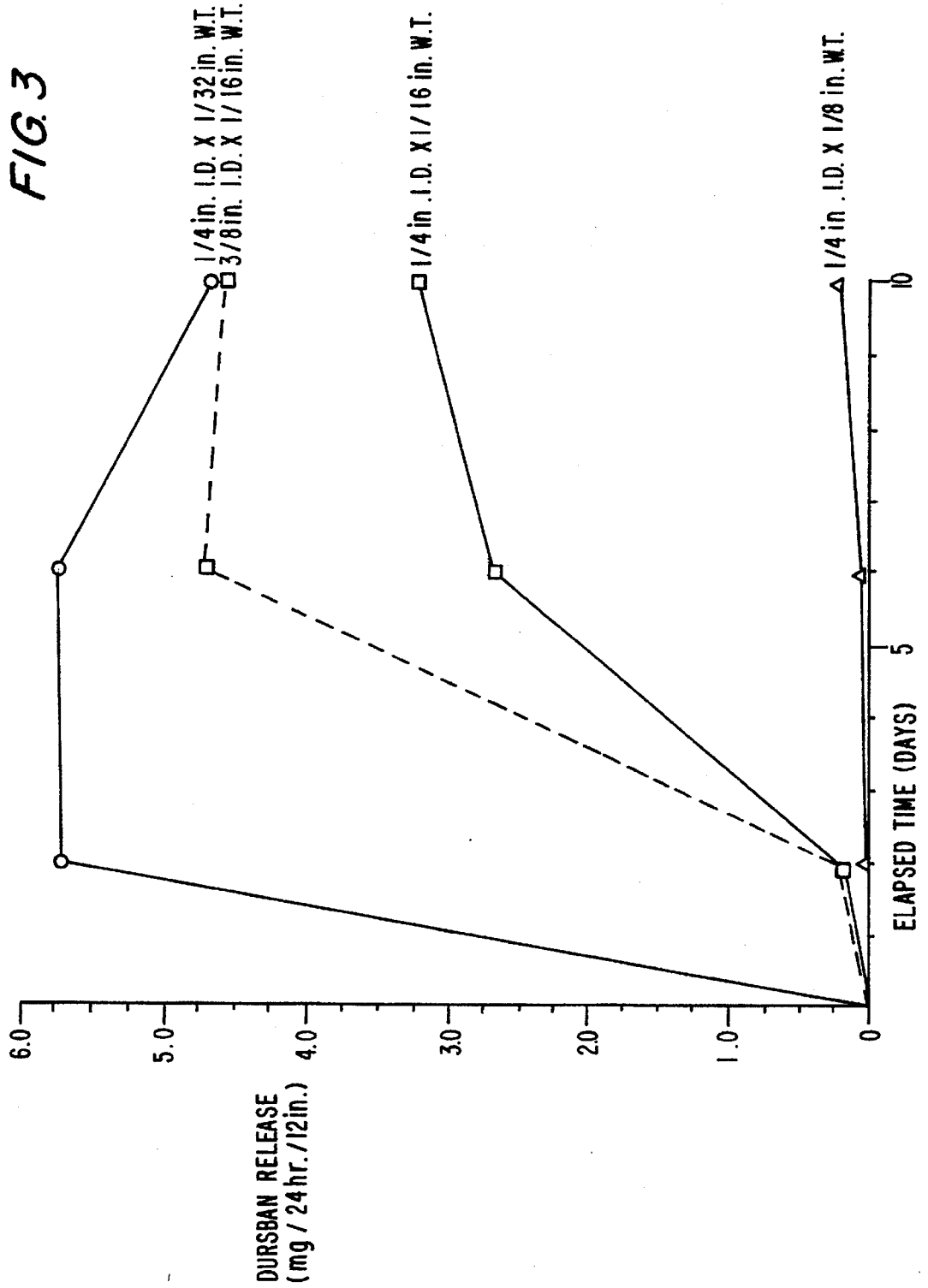
FIG. 3 is a line graph comparing Dursban® pesticide release versus time for PVC tubing reservoirs of various internal diameters (I.D.) and wall thicknesses (W.T.) containing 10 weight percent Dursban® pesticide in gel as described in Example 3.
Figure 4:
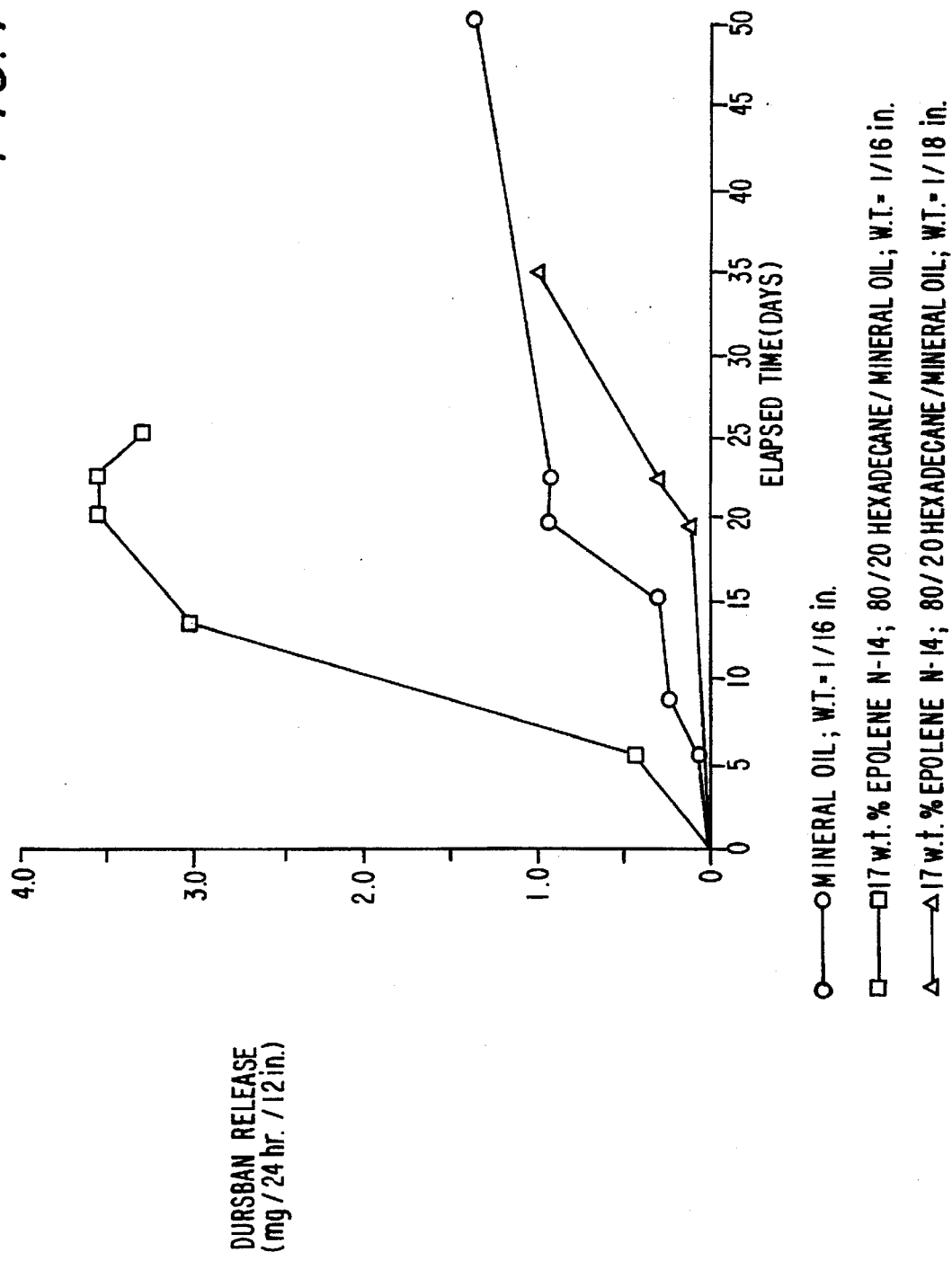
FIG. 4 is a line graph comparing Dursban® pesticide release versus time for PVC tubing reservoirs containing 10 weight percent Dursban® pesticide in (○) mineral oil (W.T.=1/16 in), (□) 17 weight percent Epolene® N-14 wax in 80/20 hexadecane/mineral oil (W.T.=1/16 in), and (Δ) 17 weight percent Epolene® N-14 wax in 80/20 hexadecane/mineral oil (W.T.=1/8 in), as described in Example 5E.

The effects of tubing wall thickness and inside diameter on the release rate of Dursban® pesticide (24°–27° C.) are illustrated in FIG. 3 for the dodecane/mineral oil/N-14 wax gel system with initial Dursban® pesticide concentration at 10 wt % and 10 cm long reservoirs. FIG. 4 tracks the Dursban® pesticide release rate (24°–27° C.) for the mineral oil solvent system for 1/16-in W.T. reservoir in comparison to the 17 wt % N-14 wax in 80/20 hexadecane/mineral oil gel matrix for 1/16-in and 1/8-in W.T. Dursban® pesticide initial concentration was 10 wt % and the reservoirs were 1/4-in I.D.×10 cm length. The data used for FIGS. 1, 2, 3, and 4 were taken from Tables VIII, IX, and X.

EXAMPLE 6

Field Studies

The following indoor field trial was performed to determine the release rate characteristics and efficacy of candidate tube reservoir collars on dogs maintained indoors.

Twenty-seven dogs of beagle breeds and different sexes were preconditioned, i.e. wormed and vaccinated for distemper, hepatitis, leptospirosis, parvovirus, and parainfluenza. After selection for health and ability to maintain parasite infestations, twenty-four dogs were subdivided into six groups of four animals, with the sexes being equally represented in each group. The dogs were housed one per pen in separate indoor pens, which were cleaned daily. Food and water were available ad libitum.

A test collar was placed around each animal's neck, such that four fingers flat can be placed between the animal's neck and the collar. The collars tested include (a) a collar with a wall thickness of 1/16 in and gel matrix with 20% Dursban® pesticide, (b) a collar with a wall thickness of 1/32 in and 20% Dursban® pesticide, (c) a collar with a wall thickness of 1/16 in and 15% Dursban® pesticide, (d) a collar with a wall thickness of 1/32 in and 15% Dursban® pesticide, and (e) a 15% diazinion collar, which is commercially available under the trademark Prevender® from Virbac corporation (France). This commercial collar is a standard, solid gel formulation. Four dogs served as an untreated control group.

One hundred (100) fleas, *Ctenocephalides felis*, and fifty (50) brown dog ticks, *Rhipicephalus sanguineus*, were applied to each dog on the specified days. At each infestation the unfed, adult parasites were placed along the dorsal midline of each dog from its head to the base of its tail. Release rate determinations were made by weighing the tubes (whole units) at timed intervals using a Mettler Balance with three decimal places. After the tubes were weighed, they were returned to their designated animals.

Efficacy against adult parasites was determined by counting the number of fleas and ticks remaining on the dogs. Dogs were combed with a flea comb until all fleas were removed from the animals. After the fleas were counted, they were placed back on the animals.

Figure 5:
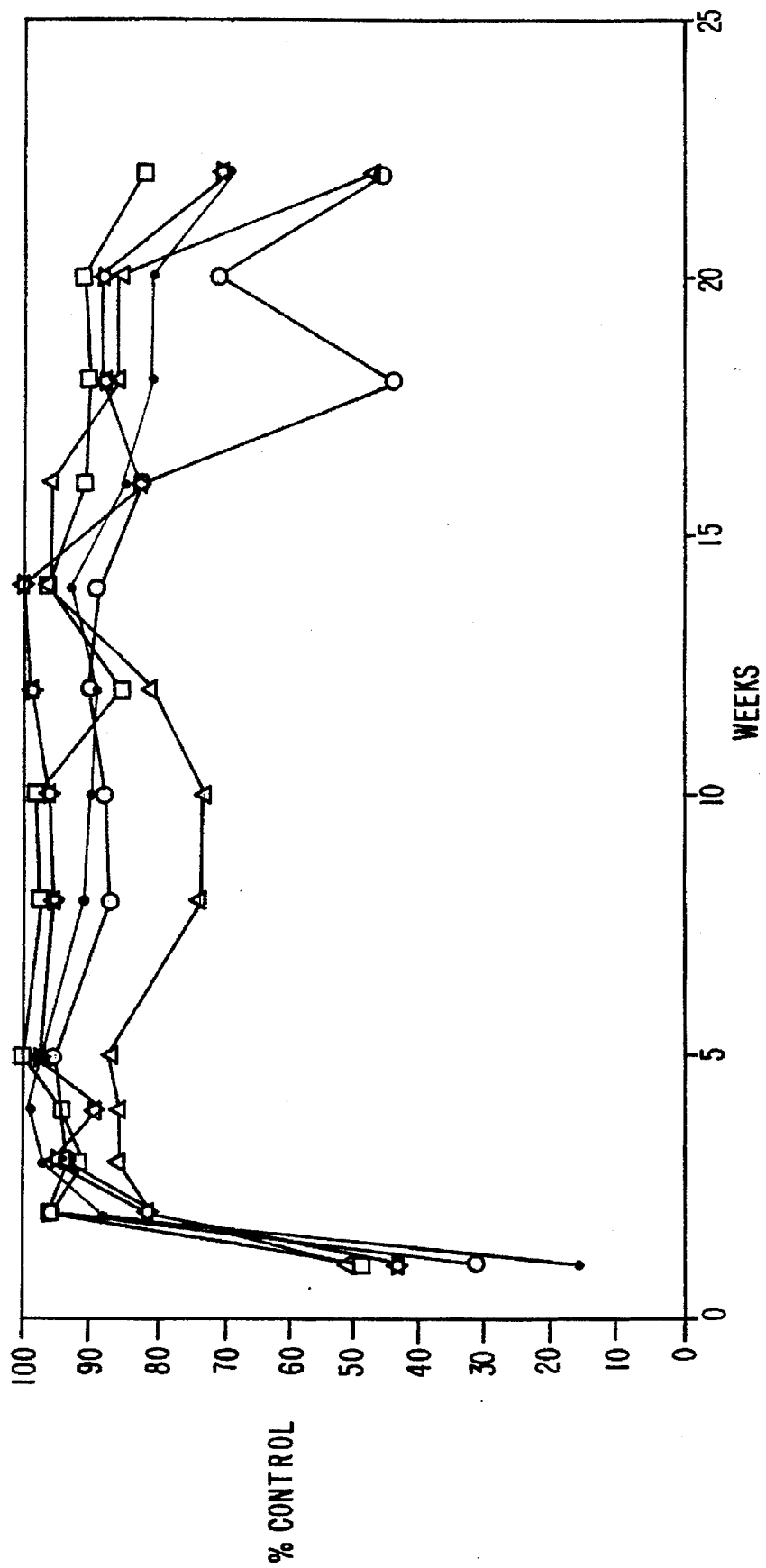
FIG. 5 is a graph comparing the effect of flea collars containing ⋈ 20% Dursban® pesticide in a 1/16 in. tube wall, ○ 20% Dursban® pesticide in a 1/16 in tube wall, a Δ15% Dursban® pesticide in a 1/32 in tube wall, □ in a 1/32 in tube wall, and ● a commercial collar. See Example 6.
Figure 6:
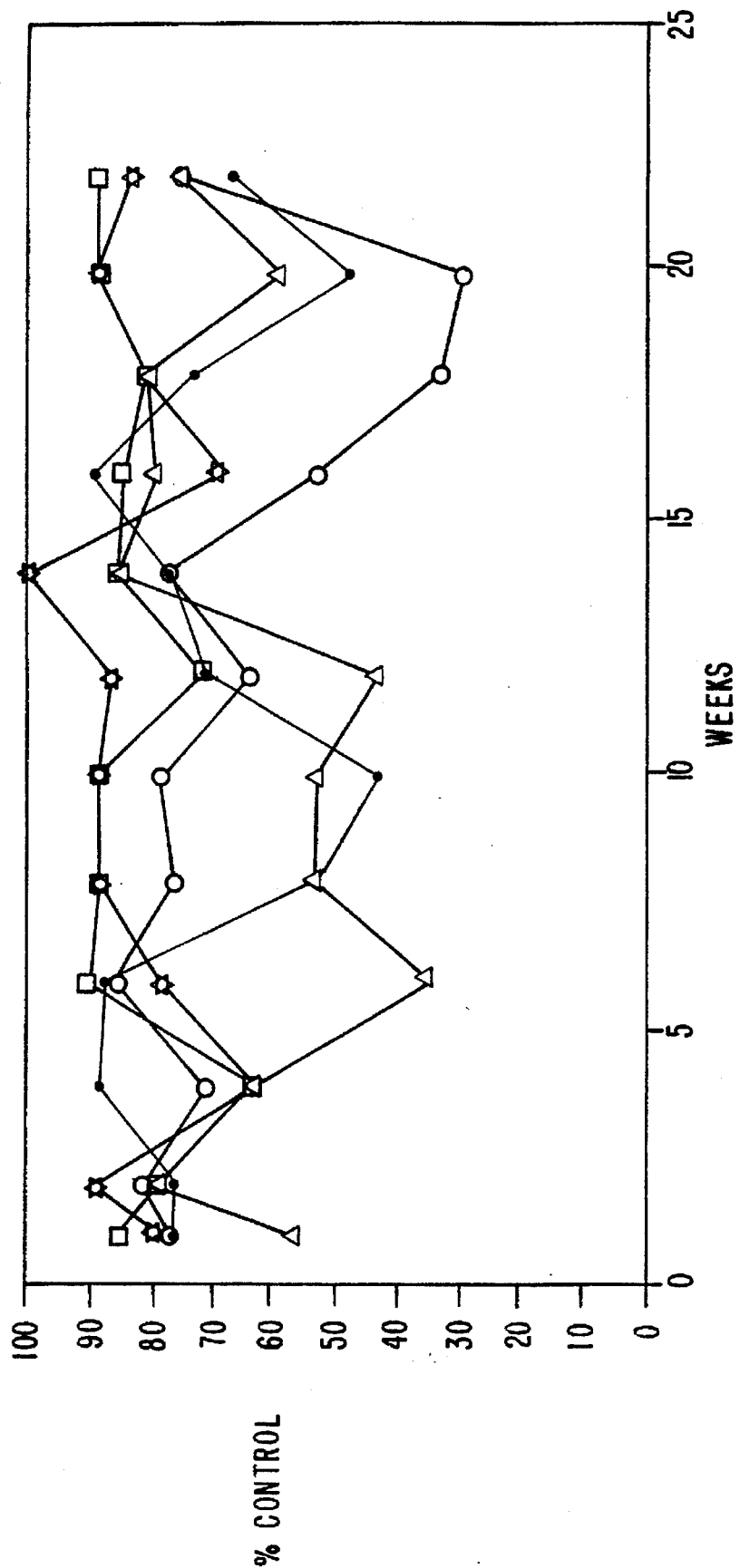
FIG. 6 is a graph comparing the effect of flea collars containing ⋈ 20% Dursban® pesticide in a 1/16 in. tube wall, ○20% Dursban® pesticide in a 1/16 in tube wall, Δ 15% Dursban® pesticide in a 1/32 in tube wall, □ in a 1/32 in tube wall, and ● a commercial collar. See Example 6.

The results of these studies are shown in FIGS. 5 and 6. These results indicate that the tube system of the invention provides comparable flea and tick protection to that obtained by a conventional collar (the 15% Diazinion collar) for approximately the first 15 weeks. However, after that time, the protection provided by the conventional collar drops off significantly, while the protection offered by the collar of the invention remains fairly consistent for about another 5–7 weeks.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A collar or ear tag device capable of the sustained controlled release of an active ingredient effective against arthropods and ectoparasites comprising a reservoir means having an inside surface defining an enclosed internal cavity and an outside surface, wherein said reservoir means is a polymeric membrane permeable to at least the active ingredient of a selected pesticidal composition, and a selected pesticidal composition comprising an organic gel matrix contained within the enclosed internal cavity of said reservoir means and in contact with the inside surface thereof, said gel matrix comprising the admixture of a gelling agent and an organic solvent and an active ingredient capable of protecting the animal against said arthropods and ectoparasites;

and a fastening means for fastening the device around the neck or to the ear of the animal.

2. The device according to claim 1 wherein said polymeric membrane is selected from the group consisting of silicone polymers, polyvinyl chloride, polyamide, flexible polyacrylate, ethylenevinylacetate, polyolefin, polyurethane, polyamide, porous tetrafluoroethylene, polyethylene, and polypropylene polymers.

3. The device according to claim 1 wherein said gelling agent is a wax selected from the group consisting of low molecular weight polyethylene waxes, paraffin waxes, hydrocarbon waxes, beeswax, animal and vegetable waxes.

4. The device according to claim 1 wherein said solvent is selected from the group consisting of n-octane, isooctane, decane, dodecane, hexadecane, mineral oil, and combinations thereof.

5. The device according to claim 1 wherein the active ingredient is an insecticide.

6. The device according to claim 5 wherein the insecticide is selected from the group consisting of chlorinated hydrocarbons, organo-phosphates, pyrethroids, and carbamates.

7. The device according to claim 5 wherein the active ingredient is selected from the group consisting of lindane, methoxyclor, permethrin, cypermethrin, dichlorvos, diazinion, dioxation, chlorfenvinphos, and bendiocarb, chlorpyrifos, amitraz, phosmet, tetramethrin, bromophos, and deltamethrin.

8. The device according to claim 1 wherein said organic gel matrix comprises about 15 to about 20 wt % of a low molecular weight polyethylene wax, about 60 to about 80 wt % of a linear aliphatic solvent, wherein upon admixture with said active ingredient, the active ingredient comprises about 10 to about 35 wt % of the gel matrix.

9. The device according to claim 1 wherein the device is capable of delivering about 0.5 mg to about 5 mg per day of said active ingredient to an animal for a period of up to about 300 days.

10. The device according to claim 3 wherein the wax is a low molecular weight polyethylene wax, and solvent is selected from the group consisting of mineral oil, and 80/20 (v/v) mixture of hexadecane and mineral oil.

11. The device according to claim 8 wherein said active ingredient is chlorpyrifos, present from about 15 to about 30 wt % of the gel matrix.

12. The device according to claim 1 wherein said insecticidal composition further comprises an insect growth regulator.

13. The device according to claim 12 wherein the regulator is selected from the group consisting of methoprene, hydroprene, S-methoprene, S-hydroprene, dimilin, and chromazine.

14. A method for protecting an animal against arthropods, comprising the step of fastening a collar or ear tag for the controlled, sustained release of an active ingredient onto the neck or to the ear of the animal, said collar or ear tag comprising:

a reservoir means having an inside surface defining an enclosed internal cavity and an outside surface, wherein said reservoir means is a polymeric membrane permeable to at least the active ingredient of a selected pesticidal composition, and a selected pesticidal composition comprising an organic gel matrix contained within the enclosed internal cavity of said reservoir means and in contact with the inside surface thereof, said gel matrix comprising the admixture of a gelling agent and an organic solvent and an active ingredient capable of protecting the animal against said arthropods; and a fastening means for fastening the device around the neck or to the ear of the animal.

15. A collar or ear tag device capable of the sustained, controlled release of an active ingredient effective against fleas and ticks comprising a reservoir means having an inside surface defining an enclosed internal cavity and an outside surface, wherein said reservoir means is polyvinyl chloride tubing permeable to at least the active ingredient of a selected pesticidal composition, and a selected pesticidal composition comprising an organic gel matrix contained within the enclosed internal cavity of said reservoir means and in contact with the inside surface thereof, said gel matrix comprising the admixture of a low molecular weight polyethylene wax and an organic solvent selected from the group consisting of mineral oil and a 80/20 (vol/vol) mixture of hexadecane/mineral oil, said active ingredient being chlorpyrifos; and a fastening means for fastening the device around the neck or of the ear of the animal.

* * * * *